United States Patent
Bronshtein

(10) Patent No.: US 11,400,051 B2
(45) Date of Patent: Aug. 2, 2022

(54) METHOD FOR PRESERVING BIOPHARMACEUTICALS

(71) Applicant: Universal Stabilization Technologies, Inc., San Diego, CA (US)

(72) Inventor: Victor Bronshtein, San Diego, CA (US)

(73) Assignee: Universal Stabilization Technologies, Inc., San Diego, CA (US)

( * ) Notice: Subject to any disclaimer, the term of this patent is extended or adjusted under 35 U.S.C. 154(b) by 278 days.

(21) Appl. No.: 16/630,421

(22) PCT Filed: Jul. 11, 2018

(86) PCT No.: PCT/US2018/041626
§ 371 (c)(1),
(2) Date: Jan. 10, 2020

(87) PCT Pub. No.: WO2019/014338
PCT Pub. Date: Jan. 17, 2019

(65) Prior Publication Data
US 2021/0145751 A1    May 20, 2021

Related U.S. Application Data

(60) Provisional application No. 62/604,591, filed on Jul. 11, 2017.

(51) Int. Cl.
| | |
|---|---|
| *A61K 9/16* | (2006.01) |
| *A61K 39/145* | (2006.01) |
| *A61K 39/15* | (2006.01) |
| *C12N 7/00* | (2006.01) |
| *A61K 39/00* | (2006.01) |

(52) U.S. Cl.
CPC .......... *A61K 9/1682* (2013.01); *A61K 9/1617* (2013.01); *A61K 9/1623* (2013.01); *A61K 9/1641* (2013.01); *A61K 39/145* (2013.01); *A61K 39/15* (2013.01); *C12N 7/00* (2013.01); *A61K 2039/5254* (2013.01); *C12N 2720/12334* (2013.01); *C12N 2760/16034* (2013.01)

(58) Field of Classification Search
None
See application file for complete search history.

(56) References Cited

U.S. PATENT DOCUMENTS

| | | | | |
|---|---|---|---|---|
| 2007/0186437 | A1* | 8/2007 | Gasteyer | A61P 37/04 34/287 |
| 2008/0229609 | A1* | 9/2008 | Bronshtein | C12N 1/04 34/92 |

* cited by examiner

Primary Examiner — Shanon A. Foley
Assistant Examiner — Myron G Hill
(74) Attorney, Agent, or Firm — CP Law Group PC; Cy Bates

(57) ABSTRACT

The disclosure concerns methods for executing PBV protocols to preserve biopharmaceuticals using a conventional lyophilizer. Also described are steps for maintaining isolation of a biopharmaceuticals for achieving aseptic drying using the conventional lyophilizer. As a collateral benefit, the invention provides good manufacturing practice (GMP) compliant methods for achieving aseptic drying of biopharmaceutical compositions using a conventional lyophilizer disposed outside of a clean-room area. Finally, methods and formulations str disclosed for preserving biopharmaceuticals suitable for mucosal or transdermal delivery to a patient.

25 Claims, 5 Drawing Sheets

METHOD FOR PRESERVING BIOPHARMACEUTICALS (i) providing an aqueous preservation composition within a container, the preservation composition including one or more biopharmaceuticals;

(ii) placing the container and preservation composition therein on a temperature-controlled shelf within a vacuum chamber of a lyophilizer, wherein the temperature-controlled shelf is adapted to provide a shelf-temperature and the vacuum chamber is adapted to provide a vacuum-pressure therein;

(iii) decreasing the shelf-temperature below 0°C and decreasing the vacuum-pressure below 1.0 Torr thereby transforming the preservation composition into a two-phase slush state, wherein the preservation composition comprises ice crystals in the two-phase slush state;

(iv) increasing the shelf-temperature above 0°C and maintaining the vacuum-pressure below 1.0 Torr thereby transforming the preservation composition into a mechanically-stable glassy foam; and

(v) increasing the shelf-temperature above 40°C for increasing the glass transition temperature of the mechanically-stable glassy foam.

*FIG.1*

| Milling Time | Wt. % of passing particles | Pictures of particles that did not pass through the sieve | Pictures of particles that passed through the sieve |
|---|---|---|---|
| 0 minutes | 0.0% | | |
| 45 minutes | 38.5% | | |
| 75 minutes | 89% | | |
| 90 minutes | 97.3% | | |

FIG.2

METHOD FOR PRESERVING BIOPHARMACEUTICALS

TECHNICAL FIELD

This invention relates generally to biopharmaceuticals; and more particularly, to improved methods for preserving biopharmaceuticals using a conventional lyophilizer.

BACKGROUND ART

The field related to biopharmaceutical preservation techniques has recently advanced and achieved significant improvement with the advent of certain distinguished methods known as "Preservation by Vaporization (PBV)" as disclosed in U.S. Pat. No. 9,469,835, issued Oct. 18, 2016.

At present, conventional lyophilizers (freeze-dryers) are not designed for executing preservation of biopharmaceuticals and other compositions using PBV protocols.

In addition, conventional freeze-drying protocols often expose biopharmaceutical compositions to extreme low temperatures which tend to impact activity of these compositions.

Because many laboratories and industrial facilities possess a conventional freeze-dryer, biopharmaceutical compositions are typically preserved using antiquated protocols, such as conventional freeze-drying, which yields lower activity and stability of the product.

SUMMARY OF INVENTION

Technical Problem

There is a need for improved methods for preserving biopharmaceuticals using conventional lyophilizers.

More particularly, there is a need for improved methods that integrate the use of a conventional lyophilizer for preserving biopharmaceuticals in accordance with PBV technology.

Additionally, there is a need to maintain aseptic isolation of biopharmaceutical compositions when preserving biopharmaceuticals in accordance with these methods.

Unique preservation formulations will be required to protect biopharmaceutical compositions during execution of PBV protocols.

Solution to Problem

The disclosure concerns methods for executing PBV protocols to preserve biopharmaceuticals using a conventional lyophilizer.

The disclosure also concerns steps for maintaining isolation of a biopharmaceuticals for achieving aseptic drying using the conventional lyophilizer.

In addition, the disclosure concerns good manufacturing practice (GMP) compliant methods for achieving aseptic drying of biopharmaceutical compositions using a conventional lyophilizer disposed outside of a clean-room area.

Finally, the disclosure concerns methods and formulations for production of ambient temperature stable micronized biopharmaceuticals suitable for mucosal or transdermal delivery to a patient.

These and other solutions to problems will be appreciated by one having skill in the art upon a thorough review of the appended descriptions, drawings and claims.

Advantageous Effects of Invention

Preservation by Vaporization (PBV) is a preferred technique in the field of biopharmaceutical preservation technologies because the process leverages concurrent boiling of water, sublimation of ice crystals, and evaporation in order to achieve a relatively mild environment during initial drying, also referred to as the "primary drying" step, which is the step where most of the water is removed from a preservation composition. The mild environment is particularly gentle on sensitive proteins, viruses, bacteria and other cellular items and could be applied for stabilization of vaccines, blood and microbiome components at ambient temperatures. Subsequent progressive drying (also known as "secondary drying") subtly increases glass transition temperature of the preservation composition such that a mechanically-stable amorphous dry glassy foam is achieved, wherein the biopharmaceuticals encapsulated within the foam are protected and preserved for (i) storage in excess of ninety days ("long-term storage"), and (ii) sometime later, for reconstitution or delivery to a patient. The disclosed methods allow the skilled artisan to preserve biopharmaceuticals in accordance with PBV protocols adapted for execution using a conventional lyophilizer. As such, no specialized equipment is necessary to preserve biopharmaceutical compositions using PBV technology.

Biopharmaceutical compositions that are preserved using PBV technology yield superior efficacy compared with the same compositions preserved using conventional freeze-drying techniques. It is conceived that extreme temperatures experienced using conventional freeze-drying techniques tend to destroy protein epitopes and useful components of these compositions such as to render the yielded product inferior to PBV-preserved compositions.

GMP production of biopharmaceutical compositions, such as but not limited to vaccines, can be achieved using the methods disclosed herein. In fact, the methods provide for improved and more efficient GMP-compliant processing of materials for stabilization for industrial applications.

Certain preservation formulations and protocols are disclosed which protect biopharmaceuticals during preservation, and which prevent devitrification of materials.

Other advantageous effects will be recognized by one with ordinary skill in the art upon a thorough review hereof.

BRIEF DESCRIPTION OF DRAWINGS

FIG. 1 shows a method for preserving biopharmaceuticals.

FIG. 2 shows a results chart related to an experiment testing activity of PBV LAIV after micronization and subsequent storage.

DESCRIPTION OF EMBODIMENTS

Figure 3:
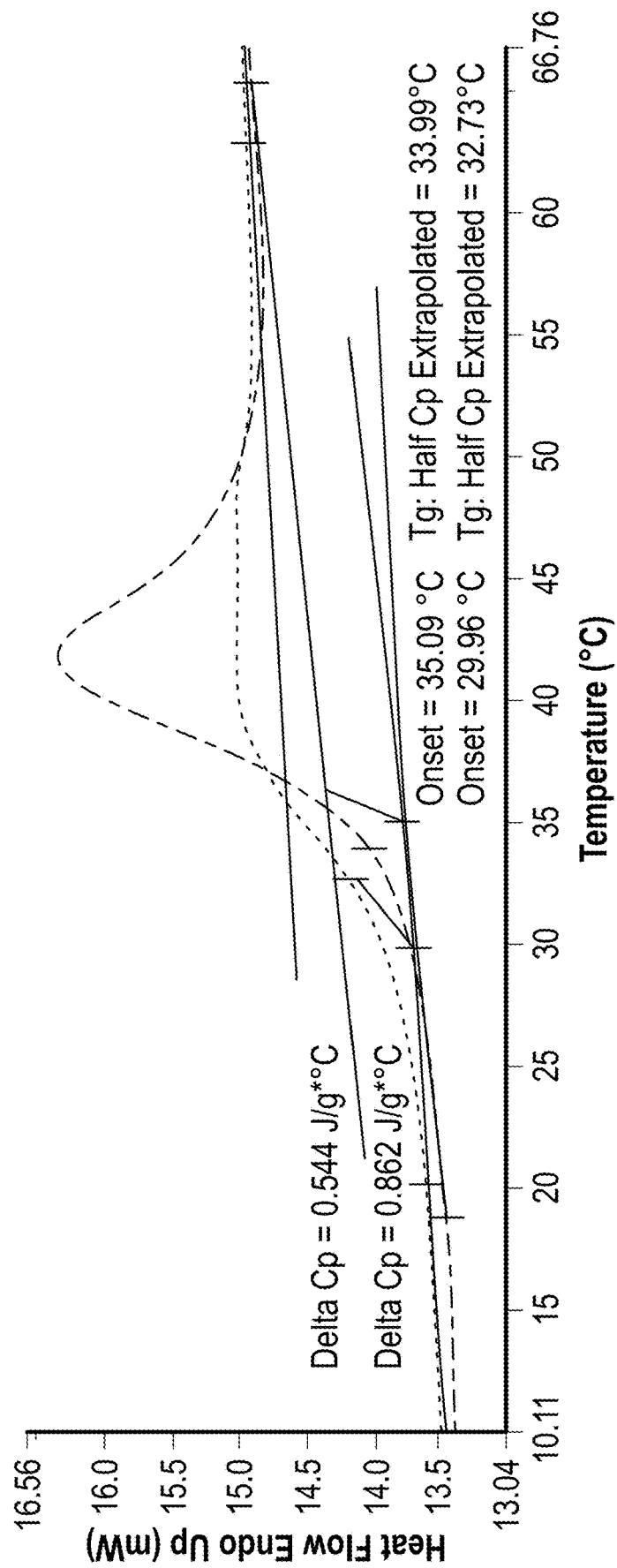
FIG. 3 shows a DSC plot associated with one experiment detailed herein.
Figure 4:
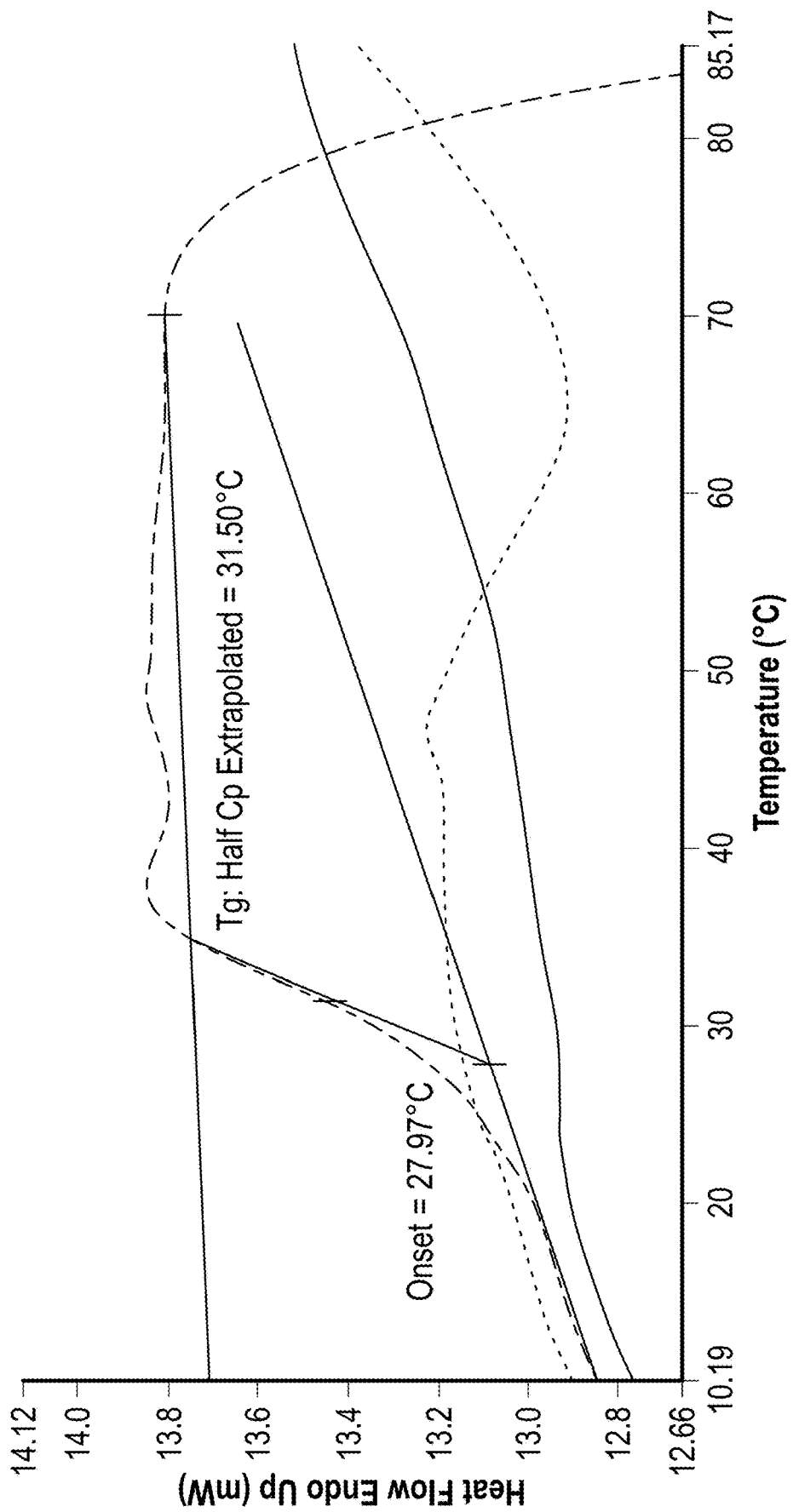
FIG. 4 shows a DSC plot associated with another experiment detailed herein.
Figure 5:
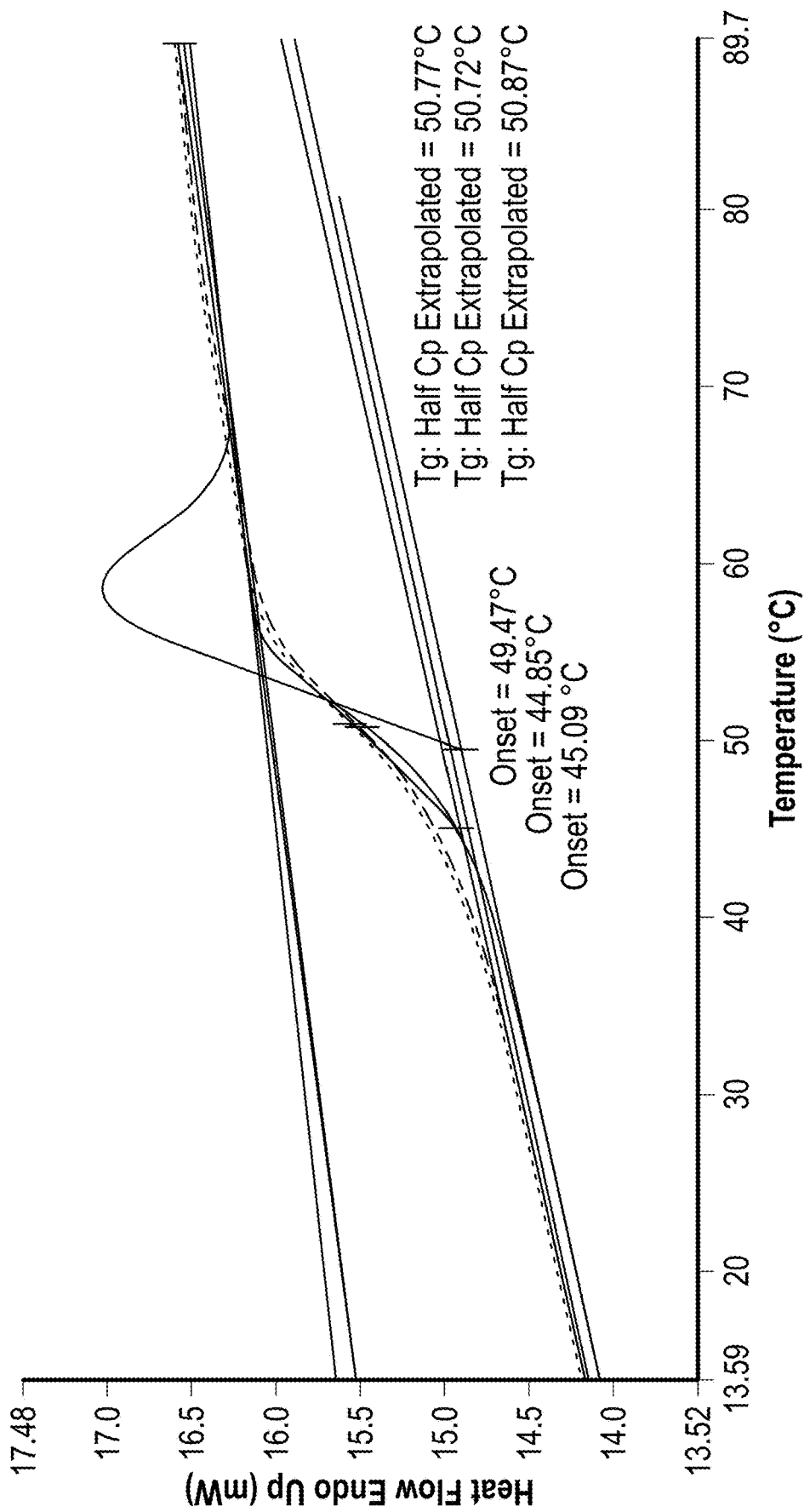
FIG. 5 shows a DSC plot associated with another experiment detailed herein.

For purposes of explanation and not limitation, details and descriptions of certain preferred embodiments are hereinafter provided such that one having ordinary skill in the art may be enabled to make and use the invention in its various aspects and embodiments. These details and descriptions are representative only of certain preferred embodiments, however, and a myriad of other embodiments which will not be expressly described will be readily understood by one having skill in the art upon a thorough review of the instant disclosure. Accordingly, any reviewer of the instant disclosure should interpret the scope of the invention by the claims, as such scope is not intended to be limited by the embodiments described and illustrated herein.

Now, in a general embodiment, a method for preserving biopharmaceuticals is disclosed. The method comprises in order the following steps:

Step (i): providing an aqueous preservation composition within a container, the preservation composition including one or more biopharmaceuticals;

Step (ii): placing the container and preservation composition therein on a temperature-controlled shelf within a vacuum chamber of a lyophilizer, wherein the temperature-controlled shelf is adapted to provide a shelf-temperature and the vacuum chamber is adapted to provide a vacuum-pressure therein;

Step (iii): decreasing the shelf-temperature below 0° C. and decreasing the vacuum-pressure below 1.0 Torr thereby transforming the preservation composition into a two-phase slush state, wherein the preservation composition comprises ice crystals in the two-phase slush state;

Step (iv): increasing the shelf-temperature above 0° C. and maintaining the vacuum-pressure below 1.0 Torr thereby transforming the preservation composition into a mechanically-stable glassy foam; and Step (v): increasing the shelf-temperature above 40° C. for increasing the glass transition temperature of the mechanically-stable glassy foam.

For purposes herein, the term "preservation composition" generally means a composition for preserving biopharmaceuticals for long-term storage at ambient temperatures from −30° C. to +40° C. and subsequent reconstitution or delivery to a patient. The preservation composition generally comprises one or more sugars and one or more biopharmaceuticals, wherein the biopharmaceuticals may comprise one or more bacteria, one or more viruses, one or more proteins, or a combination thereof. The preservation composition is aqueous in its initial state, i.e. it is a liquid or gel with some percentage composition of water greater than one percent. In this initial state, various components such as the biopharmaceuticals, sugars, sugar alcohols, and other components are selected and mixed together. However, during the initial drying step of a PBV protocol, also known as "primary drying", water is removed via concurrent boiling, evaporation and sublimation from the aqueous composition under vacuum pressure. Thus, the preservation composition, subsequent to primary drying, will be mostly devoid of water and will generally embody an amorphous dry glassy matrix or foam (herein "mechanically-stable glassy foam") with the biopharmaceuticals immobilized therein.

Accordingly, and also for purposes herein, the term "mechanically stable glassy foam" means the preservation composition post-PBV primary drying, wherein the preservation composition is substantially devoid of water and forms an amorphous dry glassy foam having a mechanical strength sufficient to maintain structural form. In particular, during PBV preservation, as soon as boiling of the preservation composition begins, bubbles nucleate and grow inside the composition, which early in the process will be a moving (not stable) foam, until the viscosity of the composition as a result of dehydration prevents the water vapor bubbles from further growth, and the bubbles are immobilized inside the composition near the end of primary drying or when most of the water is vaporized and the foam becomes mechanically-stable.

In one embodiment, during step (iv) the shelf-temperature is increased above 20° C. and the vacuum-pressure is decreased below 0.3 Torr within the vacuum chamber of the lyophilizer.

In other embodiments, during step (iv) the shelf-temperature is increased above 20° C. and the vacuum-pressure is decreased below 0.3 Torr within the vacuum chamber for a first duration, and subsequent to the first duration the shelf-temperature is increased above 30° C. and the vacuum-pressure is maintained below 0.3 Torr within the vacuum chamber.

In some embodiments, during step (v) the shelf-temperature is increased above 50° C.

In various embodiments, the aqueous preservation composition (before primary drying) comprises a liquid or a gel.

The gel can be produced by chemical crosslinking between polymers included in preservation solutions or between polymers and other molecules or ions. The ions may comprise cations, i.e. Ca++, or anions.

The gel can be produced by chemical crosslinking during warming of mixtures of frozen drops containing separate crosslinking components. The frozen drops can be produced using cryo-palletization, for example, spraying the solution in cryo-liquid such as liquid nitrogen (LN2).

The gel can also be produced by cooling of preservation compositions that turn to a gel below 0° C.

In some embodiments, cooling of polymeric solutions which can foam into gel during cooling is performed by cryo-pelletization. Cryo-pelletization is the process in which before cooling the material is dispersed into many drops.

While numerous formulations are possible, the preservation composition generally comprises: one or more non-reducing sugars, one or more sugar alcohols, or a combination thereof.

In some embodiments, at least one of said one or more non-reducing sugars is selected from the group consisting of: sucrose, trehalose, raffinose, methylglucoside, and 2-deoxyglucose. However, other non-reducing sugars known to one having skill in the art may be similarly implemented.

In some embodiments, at least one of said one or more sugar alcohols is selected from the group consisting of: mannitol, isomalt, sorbitol, and xylitol. However, other non-reducing sugars known to one having skill in the art may be similarly implemented.

The preservation composition may comprise: one or more intracellular cryo-protectors, one or more extracellular cryo-protectors, or a combination thereof.

In some embodiments, at least one of the one or more intracellular cryo-protectors is selected from the group consisting of: glycerol, propylene glycol, erythritol, sorbitol, mannitol, methylglucoside and polyethylene glycol.

In some embodiments, at least one of the one or more extracellular cryo-protectors is selected from the group consisting of: glutamic acid, glycine, proline, serine, threonine, valine, arginine, alanine, lysine, cysteine, polyvinyl pyrrolidone, polyethylene glycol, and hydroxyethyl starch.

The preservation composition may further comprise one or more antifoaming agents.

In some embodiments, at least one of the one or more antifoaming agents is selected from the group consisting of: polypropylene glycol and ethylene glycol.

In certain embodiments, the method may further comprise, prior to step (i), loading the biopharmaceuticals with one or more permeating intracellular cryo-protectors and subsequently mixing the loaded biopharmaceuticals with a preservation solution to form the preservation composition.

The one or more biopharmaceuticals comprises: a bacterium, a virus, a protein, or a combination thereof.

In one embodiment, the one or more biopharmaceuticals comprises a combination of one or more bacteria, one or more viruses, and one or more proteins.

In various embodiments, the container may comprise one of: a serum vial, a plastic bottle, a metal container, or a tray.

In some embodiments, the container may comprise a porous membrane having a pore size less than or equal to 0.25 µm, and the preservation composition may be isolated from an environment of the vacuum chamber via the porous membrane. The porous membrane may comprise any conventional filter used for sterilization of aqueous solutions.

In some embodiments, the container is also sealed within a sterilization pouch.

In some embodiments, the container may house a plurality of metallic or ceramic balls which are provided within a volume of the container along with the preservation composition.

In some embodiments, the method further comprises, subsequent to step (v), milling the mechanically-stable glassy foam within the container using the metallic or ceramic balls contained therein ("ball-milling") to transform the mechanically-stable glassy foam into particles/powder.

In some embodiments, in particular where the biopharmaceuticals are intended for mucosal or transdermal delivery, the preservation composition may comprise at least five-parts disaccharides to one-part sugar alcohols. In addition, the preservation composition may further comprise water-soluble amino acids or salts thereof. In some embodiments, the water-soluble amino acids or salts thereof may comprise: arginine, glutamic acid, glycine, proline, or a combination thereof.

In another aspect, a method for aseptic production of thermostable biopharmaceuticals is disclosed. The method comprises the following steps:

within a first area of a clean room: placing a preservation composition inside a container, the preservation composition comprising one or more biopharmaceuticals; sealing an opening of the container with a porous membrane to form a membrane-sealed container, wherein the porous membrane comprises a hole size that is less than or equal to 0.25 microns; and placing the membrane-sealed container within a sterile medical-grade sterilization pouch and heat-sealing the sterilization pouch;

exporting the sterilization pouch and membrane-sealed container therein from the first area of the clean room to a second area, wherein the method further comprises: placing the sterilization pouch and membrane-sealed container therein on a temperature-controlled shelf within a vacuum chamber of a lyophilizer; adjusting vacuum-pressure and shelf-temperature to execute a drying protocol, wherein the drying protocol comprises transforming the preservation composition into a mechanically-stable glassy foam; and subsequent to executing the drying protocol, removing the membrane-sealed container from the sterilization pouch prior to returning the membrane-sealed container to the first area of the clean room, wherein in the first area of the clean room the method further comprises: replacing the porous membrane with a sterile cup or covering the filter with a water-impermeable sterile sticker to ensure that the mechanically-stable glassy foam within the container remains isolated from external humidity during subsequent storage; and optionally transforming the mechanically-stable glassy foam within the container into a powder.

Clean rooms are typically designed to include three areas which are often referred to as: A, B, and C. A is the first and the most sterile part of the clean room. According to FDA regulations individuals can do some work or may be present outside of the area A (in B and C areas) of a clean room if they covered with clean dress and or/and covers. Individuals are not allowed in the cleanest area A. Only hands covered with sterile gloves are allowed for a short period of time to cross the line separating A area from B area to execute small operations, like delivery of a bottle or instrument inside the area A, or open or close a container or similar. Before a tool or bottle could be moved inside area A they should be isolated from environment while outside of the area A. For example, they should be placed inside a sterile pouch which will be removed before placing a tool or bottle in the area A to ensure that the area A remains sterile.

In various embodiments, the dry foam accrues as a result of nucleation and growth of vapor bubbles during boiling and appears as a bubbly foam that formed during drying of a liquid, or may appear as a dry hydrogel containing gas inclusions.

These and other embodiments are conceived and supported in accordance with the following experimental examples, wherein:

Example 1: Preservation by Vaporization (PBV)

Preservation by Vaporization (PBV) is a relatively new technique for stabilization of fragile vaccines and other biopharmaceuticals at ambient temperatures (AT). PBV execution requires simultaneous control of temperature and vacuum pressure. This could be done by contacting a drying chamber to a source of vacuum and providing heat to drying specimens to combat cooling resulting from water vaporization. The source of heat could be electromagnetic heating or conventional heat flow from a heating shelf on which the specimen is placed during drying. There could be many designs of the vacuum drying equipment that can execute the PBV process. PBV may also be executed using a conventional lyophilizer, for example, from those that are currently used for production of dry biologics using freeze-drying protocols. Because execution of freeze-drying typically requires using relatively high vacuum, conventional lyophilizers are not build to control vacuum pressure automatically if the pressure inside drying chamber is above 1 Torr, or in some cases above 2 Torr. This limits scope of PBV processes that could be automatically executed using conventional lyophilizes. However, in various embodiments herein, it is disclosed how conventional lyophilizers could be used to preserve biopharmaceuticals at ambient temperatures, and how the drying protocol could be programmed to automatic execution of PBV protocols without involvement of an operator which will be needed for GMP production and FDA approval and approval of various regulatory bodies outside the United States.

According to PBV technology, the primary drying should be performed from a partially frozen slush state. Thus, to execute PBV for a given preservation composition, such as a specimen including a preservation mixture (PM) of a biological suspension with a preservation solution (PS), or a hydrogel comprising biologics and PS, should first be partially frozen. Frozen means that there are ice crystals formed inside the specimen. Partially frozen means that the specimen temperature is at least 10° C. above Tg', where Tg' is the temperature below which the preservation composition is in solid state comprising crystallized solids and amorphous solids (glass) with no liquid phase remaining. One key difference between PBV and conventional freeze-drying is that the temperature of the specimen should be at or below Tg' during primary freeze-drying (or lyophilization). However, the specimen temperature during PBV primary drying step should be at least 10° C. above Tg' to ensure presence of the liquid phase between ice crystals. Also, to ensure that this liquid not only evaporates but also boils, the vacuum pressure in the chamber should be below equilibrium water vapor pressure above the liquid. Here, in agreement with generally accepted terminology, the primary drying is defined as an initial drying step during which the sample loses approximately 90% of initial water amount in the sample.

Prior to PBV preservation, the biopharmaceuticals should be mixed with preservation solutions (PS) designed to protect biopharmaceuticals from damaging effects of freezing and drying. Proper selection of PS is important to ensure the success of the preservation. The lower the freezing temperature, the more it is important to include conventional cryo-protectors in the PS. It is important to use both intracellular cryo-protectors that permeate inside cellular items and extracellular cryo-protectors that protect cellular and viral membranes and envelopes.

Example 2: Preservation of Animal Cells

CTV-1 is a human T-cell leukemia cell line. CTV-1 cells were grown in a 37° C., 5% CO2 incubator and cultured in suspension in RPMI media (85-90%) and heat-inactivated FBS (10-15%) with penicillin-streptomycin. Cells were split every 4-5 days and maintained at around 1E6 cells/mL. Cells were then harvested and concentrated via centrifugation to approximately 0.5-1E7 cells/mL.

Procedure: 5.5 g of cell culture were mixed 0.5 ml of 50% glycerol and loaded during 30 min at room temperature (RT). Two preservation mixtures (PM) were prepared by mixing loaded cells with twice bigger volume of two preservation solutions: PS1 containing 30% Sucrose, 15% MAG; and PS2 containing 30% Sucrose, 15% methylglucoside (MAG), and 5% polyvinyl pyrrolidone (PVP). PMs were foiled in 5 ml serum vials (0.5 ml per vials) and dried inside a freeze-drier using PBV protocol described below.

The PBV protocol used comprised the following steps:
partially freezing said PM by decreasing the shelf temperature to −18° C. and kept 18 min at −18° C.;
decreasing vacuum pressure inside the drying chamber to 0.1 Torr and keep this pressure for 5 min to ensure that the PM is frozen;
increasing the shelf temperature to 0° C. and vacuum pressure to 0.9 Torr and keep this pressure and shelf temperature for 50 min;
increasing the shelf temperature to 10° C. and decreasing the vacuum pressure to 0.5 Torr and keep this pressure and shelf temperature for 22 min;
increasing the shelf temperature to 10° C. and decreasing the vacuum pressure to 0.5 Torr and keep this pressure and shelf temperature for 22 min;
increasing the shelf temperature to 20° C. and decreasing the vacuum pressure to 0.1 Torr and keep this pressure and shelf temperature for 22 min;
increasing the shelf temperature to 30° C. and keeping the vacuum pressure to 0.1 Torr and keep this pressure and shelf temperature for 20 hours; and
increasing the shelf temperature to 40° C. and keeping the vacuum pressure to 0.1 Torr and keep this pressure and shelf temperature for 20 hours.

After preservation, PBV samples were reconstituted with 0.5 ml of with RPMI culturing media and additionally diluted 1:2 with RPMI culturing media. Cell viability was tested using the Invitrogen Tali™ image-based cytometer with the Tali™ Viability Kit—Dead Cell Red, a solution of propidium iodide. Propidium iodide is impermeant to live cells but will enter dead cells (membrane-compromised cells) and fluoresce red upon binding to nucleic acids. The Viability Kit includes the protocol that was used for the measurements: (https://tools.thermofisher.com/content/sfs/manuals/mp10786.pdf). The Talim cytometer was used to monitor cell health/viability with the propidium iodide protocol, calculate percentage of live/dead cells, and measure average cell size. Measurements on the instrument were taken with the propidium iodide fluorescence (PIF) threshold set to 440 RFU and the average cell size cutoff limited to 4-20 μm.

Results: cell survival after drying in with PS1 was below 10%; cell survival after drying with PS2 was above 75%. Thus, PVP provided protection of cellular membrane during the preservation.

Example 3: Preservation of Bacterial Cells

Suspension of bacterial cells was mixed 3:1 with 9% glycerol in PBS. After that 3 PM were prepared by mixing the suspension with twice bigger volume of 3 preservation solutions:
(PS1): Glutamic acid 7.86%, Sucrose 10%, Mannitol 5%, NaOH 2%, and PVP 4.76% adjusted to pH=7;
(PS2): Glutamic acid 7.86%, Sucrose 10%, Mannitol 5%, NaOH 2% adjusted to pH=7; and
(PS3): Glutamic acid 7.86%, Sucrose 10%, Mannitol 5%, NaOH 2%, and PEG 4.76% adjusted to pH=7.

Procedure: PMs were foiled in 5 ml serum vials (0.5 ml per vials) and dried inside a lyophilizer using the PBV protocol described below.

The PBV protocol used comprised the following steps:
partially freezing said PM by decreasing the shelf temperature to −18° C. and kept 18 min at −18° C.;
decreasing vacuum pressure inside the drying chamber to 0.1 Torr and keep this pressure for 5 min to ensure that the PM is frozen;
increasing the shelf temperature to 0° C. and vacuum pressure to 0.9 Torr and keep this pressure and shelf temperature for 50 min;
increasing the shelf temperature to 10° C. and decreasing the vacuum pressure to 0.5 Torr and keep this pressure and shelf temperature for 22 min;
increasing the shelf temperature to 10° C. and decreasing the vacuum pressure to 0.5 Torr and keep this pressure and shelf temperature for 22 min;
increasing the shelf temperature to 20° C. and decreasing the vacuum pressure to 0.1 Torr and keep this pressure and shelf temperature for 22 min; and
increasing the shelf temperature to 30° C. and keeping the vacuum pressure to 0.1 Torr and keep this pressure and shelf temperature for 20 hours.

Results: after PBV drying, the material was reconstituted with 0.5 ml of PBS and spread plated on BHI agar after serial dilutions. Plates were stored at 37° C. incubator for 24 hrs. Survival of bacteria after drying in with PS3 was below 30%; cell survival after drying with PS2 was below 60%, cell survival after drying with PS1 was above 90%. Thus, PVP provided additional protection for the bacteria during the preservation.

Example 4: Process Validation and Scaling Up Driving in Serum Vials

The studies were performed in order to validate the reproducibility of the PBV drying process. Human albumin was used as a model protein in these experiments. 2 ml of preservation mixture comprising 20 mg of recombinant human albumin (Novozymes ALBiX), 266 mg sucrose, and 133 mg isomalt were filled in 20 ml serum vials, placed on a steel tray and placed on a shelf in a lyophilizer (Freeze-drier) from Virtis. The tray was completely filled with a total number of 120 vials. PBV foam drying protocol was comprised of 3 hours of primary drying at 1500 mTorrs in temperatures ranging from −15° C. to 30° C. and 20 hours of secondary drying at 50° C. The appearance of the dry foam (mechanically-stable glassy foam) looked very consistent from vial to vial with no visible splashing.

Glass Transition Temperature (Tg) Measurement

Objective: Measure Tg of PBV albumin samples taken from different areas of the drying tray to test for uniform drying conditions in the lyophilizer.

Experimental Procedure: 5 sample vials of PBV albumin were collected from the four corners of a full drying tray (20 sample vials total). 3 DSC sample pans were prepared using dry material from each vial in a dry room. Each sample contained approximately 5 mg of manually-milled PBV foam. Sample pans were run in a DSC 8000 with Autosampler (Perkin Elmer, Massachusetts, USA). Each pan was scanned from −50° C. to 80° C. at a rate of 20° C./min, and Tg was calculated using the Pyris Data Analysis software (see example of the calculation from the below).

Results:

TABLE 1

Tg of PBV Albumin

| Group # | Group Average (Tg) |
|---|---|
| 1 | 48.18 ± 3.17° C. |
| 2 | 47.08 ± 2.07° C. |
| 3 | 49.48 ± 3.07° C. |
| 4 | 48.65 ± 1.99° C. |

Water Activity Measurements

Objective: Measure water activity (aw) from PBV albumin samples taken from different areas of the drying tray to test for uniform drying conditions in the lyophilizer.

Experimental Procedure: 5 sample vials of PBV albumin were collected from the four corners of a full drying tray (20 sample vials total). PBV foam in each vial was manually milled into powder. Approximately 150 mg of powder from each vial was tested in an Aqualab 4TE Dewpoint Water Activity Meter (Decagon Devices, Washington, USA) placed in the dry room.

Results:

TABLE 2 water activity of PBV Albumin

| Group # | Group Average ($a_w$) |
|---|---|
| 1 | 0.1287 ± 0.0060 |
| 2 | 0.1290 ± 0.0012 |
| 3 | 0.1319 ± 0.0017 |
| 4 | 0.1305 ± 0.0032 |

Example 5: Drying Inside 1-Liter Plastic Bottles Covered and Isolated from the Chamber Environment with 0.2 μm Sterilization Filter (Membrane)

PM was prepared similar to that in the previous example and filled in 1-liter plastic containers 150 g/container. After preparation of PM, each container was covered with a 0.2 μm filter used for sterilization of aqueous solutions.

The shelf temperature was decreased to −18° C., after that vacuum pressure was decreased below 0.1 Torr and kept equal to 0.1 torr to the end of the process. Next, the shelf temperature was increased to 30° C. and kept at 30° C. for 24 hours. Then, the shelf temperature was increased to 40° C. and kept at 40° C. for 24 hours.

Example 6: Preservation of Live Attenuated Influenza Vaccine (LAIV)

A single high-titer stock of frozen LAIV strain (A/17/Texas/2012/30 (H3N2)) was preserved using Preservation by Vaporization (PBV) technology. For preservation, LAIV was thawed and mixed 1:1 with different preservation solutions (PS) with pH 7 to form the preservation mixtures (PM). PMs were distributed into serum vials and dried using the PBV process with secondary drying temperatures of 45° C. and 50° C. Testing of the activity of different vaccine preparations was done using a modified LAIV TCID50 assay protocol provided by the CDC.

Experiment Flu-1:

In Experiment Flu-1 we used 7 different PS comprising:

PS1: sucrose 30%, methyl glucoside (MAG) 10%, gelatin 0.5%;

PS2: sucrose 30%, methyl glucoside (MAG) 1140%, albumin 0.5%;

PS3: sucrose 30%, mannitol 10%;

PS4: sucrose 30%, mannitol 10%, gelatin 0.5%;

PS5: sucrose 30%, acetoglucose 10%;

PS6: sucrose 30%, acetoglucose 10%, gelatin 0.5%; and

PS7: sucrose 30%, MAG 10%.

Unfortunately, PS6 crystallized out during drying and was not subsequently studied. We hypothesize that solution PS6 was supersaturated and gelatin somehow affected nucleation of acetoglucose crystals.

Results: Activity ($\log_{10}$ of $TCID_{50}$/ml) of dried vaccine after PBV and subsequent 1.6 years of storage at room temperature (RT) are shown in the table below.

TABLE 3

Activity of Dried Vaccine after PBV & Storage

| Formulation | After 1.6 years at RT |
|---|---|
| PS1 | 7.35 |
| PS2 | 7.51 |
| PS3 | 7.26 |
| PS4 | 7.43 |
| PS5 | 7.35 |
| PS7 | 7.1 |
| Frozen control | 8.8 |

Experiment Flu-2:

In Experiment Flu-2 we used PS containing a lower concentration of mannitol (33% sucrose+7% mannitol) and the 50° C. secondary drying temperature.

This experiment was performed during the time that we were first setting up and optimizing our internal TCID50 protocol, and for this reason we first measured the activity of the preserved vaccine only after 5 months of storage at RT when a reliable assay measurement was established. The vaccine titer (2E7 TCID50/ml) showed a reduction in activity of only 0.62 logs over the frozen control after PBV drying and 5 months of room temperature storage. Samples from this preparation were used in micronization studies below.

Experiment Flu-3

In Experiment Flu-3, we investigated several new formulations, including one with a further reduced mannitol concentration (35% sucrose+5% mannitol), and maintained the higher secondary drying temperature of 50° C.

Results: Activity ($TCID_{50}$/ml) of FLU-3 formulations after storage at room temperature (RT) and 37° C. are shown in the table below.

TABLE 4

Activity of FLU-3 after Storage

| Preservation Solution | After 3 months at RT Measured using | After 3 months at 37° C. optimized SOP |
|---|---|---|
| Frozen control | 8.25E+07 | 8.25E+07 |
| 15% sucrose, 10% sorbitol, 10% MgCl2, 15% MSG | 1.53E+06 | 7.11E+03 |
| 35% sucrose, 5% mannitol | 4.00E+07 | 8.62E+06 |

Conclusion: PBV drying of LAIV with 35% sucrose and 5% mannitol formulation under a process which includes a secondary drying step at 50° C. allows generation of a thermostable LAIV.

Example 7: Using Ball Milling Technology, Formulate Dry Powdered Thermostable LAIV with Particle Range Suitable for Nasal Delivery Ball Milling of PBV Dry Placebo Formulation First, we studied the ball milling of PBV formulations using placebo samples. The placebo samples were prepared and evaluated as follows:

(i) to prepare the placebo PM, 100 g of sterile cell culture media was mixed with 100 g of PS comprising 33% sucrose and 7% mannitol;

(ii) before drying, the PM was aliquoted into 20 mL serum vials (2 mL/vial);

(iii) material was subjected to the same PBV protocol which was used to dry the vaccine in early experiments, with 1 day of secondary drying at 45° C.;

(iv) after drying, the PBV placebo foam was first crushed inside serum vials with a sterile spatula to disrupt the PBV foam, decreasing the particle size to several hundred microns;

(v) subsequent micronization was performed using Lab-Wizz Laboratory-Scale Ball Mill for time periods of 45, 75, or 90 minutes at a frequency of 15 Hz—which we had previously determined to be a suitable frequency to obtain particles of about 20 microns;

(vi) powder was passed through a copper sieve of mesh size 63 μm to remove any clumps or larger particles. Portions of powder material that would not pass through the sieve were recorded. The mesh size was selected to be 63 μm because that size is specified for sieving LactoHale lactose powder, which is used as a dry powder extender in preparation of dry LAIV vaccines for respiratory delivery. We also found that particles that can pass through this mesh are substantially smaller than 63 μm and well suited for respiratory delivery; and (vii) powders were suspended in mineral oil inside the dry room and evaluated using conventional microscopy.

We have found (see table below) that ball milling of PBV foams to particle sizes adequate for respiratory delivery can be achieved using a shaking frequency of 15 Hz and milling time ranging from 45-90 minutes. Shorter milling times tend to produce more variable particle sizes, increasing the percentage of particles that do not pass through 63 μm sieve. We concluded that 75 minutes of milling at 15 Hz shaking frequency is an optimum protocol for producing micronized vaccine powders for respiratory delivery.

Results are illustrated in FIG. 2.

Activity of PBV LAIV after Micronization and Subsequent Storage.

In this part of the study we evaluated the effect of milling time on the vaccine produced in Experiment Flu-2 using PS comprising 33% sucrose and 7% mannitol. The vaccine micronization was performed as described above, that is, for the placebo samples.

Results: Activity (TCID50) per milligram of dry PBV LAIV powder micronized at 15 Hz for 45, 75, and 90 minutes, and subsequent 1.5 months of storage at 4° C., RT, and 37° C., shown below.

TABLE 5

Activity of Dry PBV LAIV micronized powder

| | Activity (TCID50/mg) | Logs of activity loss |
|---|---|---|
| PBV foam from FLU-3 before milling | 1.41E+05 | 0 |
| After 45 min of milling and 1.5 months at RT | 1.26E+05 | −0.05 |
| After 45 min of milling and 1.5 months at 4° C. | 2.55E+04 | −0.74 |
| After 45 min of milling and 1.5 months at 37° C. | 1.94E+04 | −0.86 |
| After 75 min of milling and 1.5 months at RT | 5.55E+04 | −0.40 |
| After 75 min of milling and 1.5 months at 4° C. | 4.66E+04 | −0.48 |
| After 75 min of milling and 1.5 months at 37° C. | 3.68E+03 | −1.58 |
| After 90 min of milling and 1.5 months at RT | 5.98E+04 | −0.37 |
| After 90 min of milling and 1.5 months at 4° C. | 3.84E+04 | −0.56 |
| After 90 min of milling and 1.5 months at 37° C. | 1.32E+04 | −1.03 |

Ball milling resulted in low activity loss and the micronized vaccine remained stable at RT for at least 1.5 months. However, we found significant decrease in micronized vaccine stability during storage at 37° C. compared to that of non-micronized vaccine preparations. This could be due to crystallization of mannitol or sucrose from supersaturated sucrose mannitol glass. This crystallization could be initiated by nucleation of mannitol crystals on the surface of fractures that occur during milling.

Example 8: Effect of Micronization on the PBV Preserved Live Attenuated Rotavirus Vaccine (LARV)

A LARV vaccine was mixed 1:1 with a PS comprising 30% sucrose and 10% mannitol and preserved by PBV. Similar to that of the currently-discussed Flu vaccine, particle size reduction was performed in two steps: manual milling followed by ball milling (micronization) using a Laarmann Labwizz lab-sized ball mill. First, vials that had been stored at room temperature for 3 months were opened and the dry foamed material inside the vials was manually-milled using a spatula in the dry room with 15-18% relative humidity. Approximately 120 mg of manually milled foam was recovered from each vial. The particle size after the manual milling typically was several hundred of microns. Next, the manually milled foam was placed in 2 mL metal containers containing 3×2 mm steel balls each. The containers were placed inside the ball mill and shaken at a speed of 15 Hz for 30 minutes to reduce the size of the particles to approximately 50 microns. A portion of the powders was dried under vacuum for one day at 45° C.

We found that viral activity loss after micronization and subsequent 5 months of storage at RT was very small (<0.2 logs). However, after 5 months storage at 37° C. we had lost 0.8 logs of activity which was not observed for non-micronized formulations. This observation correlates with decrease of stability of PBV flu vaccine after micronization above.

Our measurements of Tg using Differential Scanning Calorimeter supported the working hypothesis that the decrease in viral activity at 37° C. in micronized specimens could be associated with sugar crystallization from crystals nucleating on the surface of fractions.

We investigated PBV formulations prepared with PS comprising 30% sucrose and 10% mannitol. For each formulation, we prepared 3 independent specimens hermetically sealed inside aluminum pans. With non-micronized formulations, we did not see any unexpected results, and were able to measure Tg during the first, second, and third DSC runs from −50 to 80° C. See FIG. 3, which shows a DSC Scan of Rota-1 PM4 powder, hand-milled, without micronization, 3 runs.

However, for micronized powder only, the first runs of each sample pan had an observable glass transition behavior, after which we clearly observed a quick decrease in DSC output associated with crystallization during warming. This phenomenon, also known as devitrification, is often observed in metastable supersaturated mixtures above the glass transition temperature when low viscosity is not stopping growth of crystals that often form on the surface of fractions in the glass state. FIG. 4 shows DSC runs for dry micronized PM4 formulation.

Devitrification is an irreversible kinetic crystallization process in supersaturated solutions that have not crystallized during cooling and thus form stable glasses below Tg. Typically, crystallization during cooling does not happen because the nucleus of crystals forms at the temperatures below the temperature at which the crystals can grow, or the nucleation of crystals could happen only on the surface of fractures in the glass state. During warming above Tg, when the viscosity of the solution decreases, the crystal nuclei that form at lower temperatures begin to grow with speed which increases with increasing temperature-irreversibly transforming the material in the crystallized state. The higher the Tg, the higher the temperature that devitrification happens for a given warming rate.

We also measured Tg in samples of micronized dry formulation that were dried for an additional day at 45° C. under vacuum. In these samples no effect of devitrification during warming from the glass state was detected. DSC runs for dry micronized PM4 formulation after additional drying at 45° C. are shown in FIG. 5.

After additional drying of dry micronized formulation, Tg measurements were significantly higher (Tg was slightly above 50° C.) than that obtained for micronized formulation (Tg was slightly above 30° C.) that did not have an additional drying step. This explains why no devitrification was observed in the additionally dried powders.

The devitrification does not necessarily happen in all vitrification mixtures and depends on the composition of the mixture. According to our preliminary observations it is more pronounced in mixtures containing mannitol compared with mixtures containing MAG. It is contemplated herein that an increase of Tg will decrease or eliminate the devitrification.

INDUSTRIAL APPLICABILITY

The claimed invention is applicable to the pharmaceutical industry, specifically the vaccine industry though other portions of the pharmaceutical industry are also applicable.

CITATION LIST

U.S. Pat. No. 9,469,835, issued Oct. 18, 2016.

Pushkar, N. S. and V. L. Bronshtein. 1988. The mechanism of ice formation on rewarming of the frozen cryoprotectant solutions. Proc. Ukrainian Acad. Sci. 10: 68-70.

What is claimed is:

1. A method for preserving biopharmaceuticals, comprising in order the following steps:

(i) providing an aqueous preservation composition within a container, the preservation composition including one or more biopharmaceuticals;

(ii) placing the container and preservation composition therein on a temperature-controlled shelf within a vacuum chamber of a lyophilizer, wherein the temperature-controlled shelf is adapted to provide a shelf-temperature and the vacuum chamber is adapted to provide a vacuum-pressure therein;

(iii) executing a partial freezing protocol, the partial freezing protocol comprising:

decreasing the shelf-temperature below 0° C. and maintaining temperature of the preservation composition above Tg', thereby transforming the preservation composition into a two-phase slush state, wherein the preservation composition comprises ice crystals and aqueous liquid-phase in the two-phase slush state;

(iv) executing a primary drying protocol, said primary drying protocol comprising:

increasing the shelf-temperature above 0° C. and maintaining the vacuum-pressure below 1.0 Torr thereby boiling water from the preservation composition in the two-phase slush state to form a mechanically-stable glassy foam; and (v) executing a secondary drying protocol, said secondary drying protocol comprising:

increasing the shelf-temperature above 40° C. for increasing the glass transition temperature of the mechanically-stable glassy foam.

2. The method of claim 1, wherein during step (iv) the shelf-temperature is increased above 20° C. and the vacuum-pressure is decreased below 0.3 Torr within the vacuum chamber of the lyophilizer.

3. The method of claim 1, wherein during step (iv) the shelf-temperature is increased above 20° C. and the vacuum-pressure is decreased below 0.3 Torr within the vacuum chamber for a first duration, and subsequent to the first duration the shelf-temperature is increased above 30° C. and the vacuum-pressure is maintained below 0.3 Torr within the vacuum chamber.

4. The method of claim 1, wherein during step (v) the shelf-temperature is increased above 50° C.

5. The method of claim 1, wherein the aqueous preservation composition comprises a liquid or a gel.

6. The method of claim 1, wherein the preservation composition comprises: one or more non-reducing sugars, one or more sugar alcohols, or a combination thereof.

7. The method of claim 6, wherein at least one of said one or more non-reducing sugars is selected from the group consisting of: sucrose, trehalose, raffinose, methylglucoside, and 2-deoxyglucose.

8. The method of claim 6, wherein at least one of said one or more sugar alcohols is selected from the group consisting of: mannitol, isomalt, sorbitol, and xylitol.

9. The method of claim 1, wherein the preservation composition comprises: one or more intracellular cryo-protectors, one or more extracellular cryo-protectors, or a combination thereof.

10. The method of claim 9, wherein at least one of said one or more intracellular cryo-protectors is selected from the group consisting of: glycerol, propylene glycol, erythritol, sorbitol, mannitol, methylglucoside and polyethylene glycol.

11. The method of claim 9, wherein at least one of said one or more extracellular cryo-protectors is selected from the group consisting of: glutamic acid, glycine, proline, serine, threonine, valine, arginine, alanine, lysine, cysteine, polyvinyl pyrrolidone, polyethylene glycol, and hydroxyethyl starch.

12. The method of claim 1, wherein the preservation composition comprises one or more antifoaming agents.

13. The method of claim 12, wherein at least one of said one or more antifoaming agents is selected from the group consisting of: polypropylene glycol and ethylene glycol.

14. The method of claim 1, further comprising: prior to step (i), loading the biopharmaceuticals with one or more permeating intracellular cryo-protectors and subsequently mixing the loaded biopharmaceuticals with a preservation solution to form the preservation composition.

15. The method of claim 1, wherein said one or more biopharmaceuticals comprises: a bacterium, a virus, a protein, or a combination thereof.

16. The method of claim 15, wherein said one or more biopharmaceuticals comprises a combination of one or more bacteria, one or more viruses, and/or one or more proteins.

17. The method of claim 1, wherein the container is one of: a serum vial, plastic bottle, metal container, or tray.

18. The method of claim 1, wherein said container comprises a porous membrane having a pore size less than or equal to 0.25 µm, and wherein said preservation composition is isolated from an environment of the vacuum chamber via said porous membrane.

19. The method of claim 18, wherein said container is sealed within a sterilization pouch.

20. The method of claim 19 wherein a plurality of metallic or ceramic balls are provided within a volume of the container.

21. The method of claim 20, further comprising: subsequent to step (v), milling the mechanically-stable glassy foam within the container using the metallic or ceramic balls contained therein.

22. The method of claim 1, wherein the preservation composition comprises at least five-parts disaccharides to one-part sugar alcohols.

23. The method according to claim 22 wherein the preservation composition further comprises water-soluble amino acids or salts thereof.

24. The method of claim 23, wherein the water-soluble amino acids or salts thereof comprises: arginine, glutamic acid, glycine, proline, or a combination thereof.

25. A method for aseptic production of thermostable biopharmaceuticals comprising the following steps:
 i. within a first area of a clean room:
   placing a preservation composition inside a container, the preservation composition comprising one or more biopharmaceuticals;
   sealing an opening of the container with a porous membrane to form a membrane-sealed container, wherein the porous membrane comprises a hole size that is less than or equal to 0.25 microns;
   placing the membrane-sealed container within a sterile medical-grade sterilization pouch and heat-sealing the sterilization pouch;
 ii. exporting the sterilization pouch and membrane-sealed container therein from the first area of the clean room to a second area, wherein the method further comprises:
   placing the sterilization pouch and membrane-sealed container therein on a temperature-controlled shelf within a vacuum chamber of a lyophilizer;
   adjusting vacuum-pressure and shelf-temperature to execute a drying protocol, wherein the drying protocol comprises transforming the preservation composition into a mechanically-stable glassy foam;
 iii. subsequent to executing the drying protocol, removing the membrane-sealed container from the sterilization pouch prior to returning the membrane-sealed container to the first area of the clean room, wherein in the first area of the clean room the method further comprises:
   replacing the porous membrane with a sterile cup or covering the filter with a water-impermeable sterile sticker to ensure that the mechanically-stable glassy foam within the container remains isolated from external humidity during subsequent storage; and
   optionally transforming the mechanically-stable glassy foam within the container into a powder.

* * * * *